United States Patent
Bonner et al.

(12)

(10) Patent No.: US 6,362,317 B1
(45) Date of Patent: Mar. 26, 2002

(54) ANTI-γ-H2A ANTIBODY, FUSION PROTEINS THEREOF AND METHOD AND KIT FOR DETERMINING DNA DOUBLE-STRANDED BREAKS

(75) Inventors: William M. Bonner, Potomac; Emmy Rogakou, Bethesda, both of MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/351,721

(22) Filed: Jul. 12, 1999

(51) Int. Cl.$^7$ .................. C07K 16/18; C07K 14/435
(52) U.S. Cl. ...................... 530/387.1; 530/358
(58) Field of Search ................ 530/358, 350, 530/387.9, 388.1, 389.1, 387.1; 435/328

(56) References Cited

U.S. PATENT DOCUMENTS 5,637,465 A * 6/1997 Trauth
5,807,999 A * 9/1998 Kohtz

OTHER PUBLICATIONS

Rogakou et al., *Proceedings of the American Association for Cancer Research Annual*, 38 (Apr., 1997) (Abstract No. 2313).

Rogakou et al., *Proceedings of the Amercan Association for Cancer Research Annual*, 39 (Mar., 1998) (Abstract No. 3927).

Soto et al. Mapping of the linear antigenic determinants from the Leishmania infantum histone H2A recognized by sera from dogs with leishmaniasis. Immunology Letters, vol. 48, pp. 209–214, 1995.*

Muller et al. Comparison of different methods for localizing antigenic regions in histone H2A. Molecular Immunology, vol. 23(6), pp. 593–601, 1986.*

Carrier et al. Recombinant antibody–alkaline phosphatase conjugates for diagnosis of human lgGs: application to anti–HBsAg detection. Journal of Immunological Methods, vol. 181, pp. 177–186, 1995.*

Bonner et al., *Molecular Biology of the Cell*, 9, 320A (1998) (Abstract).

Mannironi et al., *Nucleic Acids Research*, 17 (22) 9113–9126 (1989).

Rogakou et al., *Molecular Biology of the Cell*, 9, 109A (1998) (Abstract).

Rogakou et al., *The Journal of Biological Chemistry*, 273 (10) 5858–5868 (1998).

Ueda et al., *Developmental Biology*, 169, 210–217 (1995).

* cited by examiner

*Primary Examiner*—John S. Brusca
(74) *Attorney, Agent, or Firm*—Leydig, Voit & Mayer, Ltd.

(57) ABSTRACT

The present invention provides an isolated or purified antibody or antigenically-reactive fragment thereof that specifically binds to a C-terminal phosphorylated serine in an H2A histone protein and a product comprising the same. The present invention further provides fusion proteins comprising the isolated or purified antibody or antigenically-reactive fragment thereof. Also provided by the present invention are a method and a kit for determining double-stranded breaks in DNA. The method comprises contacting a sample comprising H2A histone proteins with the isolated or purified antibody or antigenically-reactive fragment thereof and detecting binding of the antibody or fragment thereof to an H2A histone protein in the sample. The detection of the binding of the antibody or fragment thereof to the H2A histone protein indicates the presence of a DNA double-stranded break in DNA.

10 Claims, No Drawings

ANTI-γ-H2A ANTIBODY, FUSION PROTEINS THEREOF AND METHOD AND KIT FOR DETERMINING DNA DOUBLE-STRANDED BREAKS

TECHNICAL FIELD OF THE INVENTION

The present invention relates to antibodies, antibody fragments and fusion proteins thereof, and their use in determining DNA double-stranded breaks.

BACKGROUND OF THE INVENTION

In a normal human cell, about 2 meters of DNA are folded and packaged into a nucleus less than 10 microns in diameter. Much of this compaction is performed by wrapping the DNA around nucleosomes, which are complexes composed of histone proteins. Compaction and packaging into the nucleus provides a level of protection for fragile strands of DNA. However, despite the compaction of DNA into chromosomes, double-stranded breaks in DNA are common.

DNA double-stranded breaks jeopardize a chromosome's physical integrity essential for its correct segregation during mitosis and meiosis as well as its informational redundancy critical for maintaining accurate encoding of cellular components. Given that DNA double-stranded breaks have the potential to cause a great deal of damage to the cell, it is not surprising that multiple cellular mechanisms exist for dealing with this serious lesion, including non-homologous end joining, homologous recombination, and apoptosis. On the other hand, DNA double-strand cleavages are necessary in several important cellular processes, including recombination during meiosis and mitosis, V(D)J recombination during immune system development, and mating type switching in $S.$ $cerevisiae.$ Aside from natural processes, DNA double-stranded breaks also appear following exposure to radiation, magnetic fields, toxins, mutagenic chemicals, various medications, and the like.

While much is known about the causes and actual rejoining of DNA double-stranded breaks, much less is known about how these breaks are initially recognized. Elucidation of an organism's initial response mechanisms to double-stranded breaks would provide a means to detect DNA double-stranded breaks. Currently, DNA breaks are detected using pulsed-field electrophoresis, filter elution, sucrose gradient sedimentation, single cell gel electrophoresis or the TdT-mediated fluorescein-dUTP nick end labeling (TUNEL) assay. The former three methods are useful for only gross measurements of DNA damage in a large sample.

Single cell gel electrophoresis, also known as the comet assay, capitalizes on the movement of fragmented DNA out of a cell body into the agarose gel toward the anode during electrophoresis. The resulting shape resembles a comet, the cell body being the comet head and the fragmented DNA being the comet tail. The comet assay, frequently used in the study of apoptosis, is an improvement over the aforementioned techniques in that it allows measurement of DNA cleavage in an individual cell. However, this technique requires a great deal of time and effort to study DNA breaks in larger samples and lacks sensitivity.

The TUNEL assay employs terminal deoxynucleotidyl transferase to incorporate modified nucleotides onto free 3'-hydroxyl ends of DNA fragments. In most cases, DNA breaks are visualized by differential staining of intact and fragmented DNA. However, the TUNEL assay, as well as the comet assay, require many hundreds of DNA double-stranded breaks to yield a positive signal.

In that only a few double-stranded breaks can result in phenotypic change and 40 double-stranded breaks result in cell death, the currently available assays clearly do not have the sensitivity to be useful in all situations, particularly with non-lethal amounts of breaks. In view of the above, there exists a need for a sensitive means of determining DNA double-stranded breaks. It is an object of the present invention to provide such a means. This and other objects and advantages of the present invention, as well as additional inventive features, will be apparent from the description of the invention provided herein.

BRIEF SUMMARY OF THE INVENTION

The present invention provides an isolated or purified antibody or antigenically-reactive fragment thereof that specifically binds to a C-terminal phosphorylated serine in an H2A histone protein. The present invention further provides a fusion protein comprising the isolated or purified antibody or an antigenically-reactive fragment thereof. The present invention further provides a product useful for the determination of DNA double-stranded breaks. The product comprises the present inventive isolated or purified antibody or antigenically-reactive fragment thereof.

Also provided by the present invention are a method and a kit for determining double-stranded breaks in DNA. The method comprises contacting a sample comprising H2A histone proteins with the isolated or purified antibody or antigenically-reactive fragment thereof of the present invention and detecting binding of the antibody or antigenically-reactive fragment thereof to an H2A histone protein in the sample. The detection of the binding of the antibody or antigenically-reactive fragment thereof to an H2A histone protein indicates the presence of a double-stranded break in DNA.

The invention may best be understood with reference to the following detailed description of the preferred embodiments.

DESCRIPTION OF THE PREFERRED EMBODIMENTS

The present invention is predicated on the discovery that mammalian cells and mice respond to agents that introduce DNA double-stranded breaks with the immediate and substantial phosphorylation of histone H2AX. For many years, scientific paradigms envisioned the role of histones in chromatin and chromosomes as limited to the compaction of DNA. However, it has been discovered that H2AX is intimately involved in the recognition of regions of chromatin containing a DNA double-stranded break. The present invention seeks to capitalize on the formation of the phosphorylated H2A protein, termed γ-H2A, in order to provide a means of sensitive detection of DNA double-stranded breaks. Therefore, the present invention provides an isolated or purified antibody or antigenically-reactive fragment thereof which specifically binds to a C-terminal phosphorylated serine in an H2A histone protein and methods of use.

As used herein, an "antibody" is a protein comprising one or more polypeptides selected from immunoglobulin light chains, immunoglobulin heavy chains, and antigen-binding fragments thereof, which are capable of binding to at least one antigen. An antibody of the present invention includes intact monoclonal and polyclonal immunoglobulins. An antibody of the present invention also includes immunoglobulin types IgA, IgD, IgE, IgG, IgM and subtypes of any of the foregoing, wherein the light chains of the immunoglobulin may be kappa or lambda type. Antibodies of the present invention additionally include bifunctional antibodies in which one arm of the antibody is specific to γ-H2A and the other arm is specific for another antigen. By "isolated" is meant the removal of an antibody or antigenically-reactive fragment thereof from its natural environment. By "purified" is meant that a given antibody or fragment thereof, whether one that has been removed from nature (isolated from blood serum) or synthesized (produced by recombinant means), has been increased in purity, wherein "purity" is a relative term, not "absolute purity."

An "antigenically-reactive fragment" of an antibody includes segments of immunoglobulins that retain antigen-binding specificity, for example, Fab, Fab', F(ab')$_2$ and F(v) fragments. Preferably, the antigenically-reactive fragment retains the ability to bind selectively γ-H2A. The antibody or fragment thereof may be a single-chain antibody. The antibody or fragment thereof may be a heavy chain monomer, dimer or trimer, a light chain monomer, dimer or trimer, a dimer consisting of one heavy and one light chain, and the like.

One of ordinary skill in the art will appreciate that the isolated or purified antibody or antigenically-reactive fragment thereof of the present invention may include various deletions, additions or substitutions which either do not affect the binding affinity of the antibody or, preferably, enhances the affinity of the antibody for γ-H2A. Alterations may also include truncation of non-essential regions of the antibody, such as those not responsible for antigen binding or structure of the antibody.

The isolated or purified antibody or antigenically-reactive fragment thereof can be derived from any animal. The particular animal from which the antibody or fragment thereof is derived is not essential to the present invention. The antibody or fragment thereof may be humanized, meaning that an antibody, originally derived from an animal, is altered by substituting amino acids not involved in antigen binding with amino acids from corresponding regions of a human immunoglobulin. The use of humanized antibodies or fragments thereof limits the antigenicity of a foreign antibody.

The isolated or purified antibody or fragment thereof of the present invention specifically binds to a C-terminal phosphorylated serine in an H2A histone protein. H2A histone proteins are found in all examined species of animals. Preferably, the H2A histone protein is a mammalian H2A histone protein. More preferably, the H2A histone protein is H2AX. H2AX is one of the three types of conserved histone H2A protein species. H2AX differs from the other two H2A proteins, H2A1–H2A2 and H2AZ, by the presence of a conserved motif at the C-terminus (Mannironi et al., *Nucleic Acid Research*, 17, 9113–9125 (1989)). Preferably, the C-terminus of the H2A histone protein of the present invention comprises the amino acid sequence SQ(D/E/A)(I/L/Y/F) (SEQ ID NOS. 1). It is the phosphorylation of the serine in the motif, residue 139 in mammals, that yields the modified form named γ-H2AX.

As used herein, "C-terminal phosphorylated serine" refers to a phosphorylated serine located within about 25 amino acids of the C-terminus of the protein. Preferably, the phosphorylated serine is within about 10 amino acids of the C-terminus of the protein, more preferably within about 4 amino acids from the C-terminus of the protein.

Isolated or purified antibodies or antigenically-reactive fragments thereof directed to γ-H2A are generated using various methods well-known in the art. The present invention is not dependent on a particular method of antibody production. For example, anti-γ-H2A antibodies can be isolated or purified from serum taken from an animal immunized with γ-H2A. Immunization may be accomplished using standard procedures. The particular dose and routes of administration for an immunizing peptide, i.e., γ-H2A, depend on the type of animal, the body weight and age of the animal and its immune status. The immunizing peptide can be an intact γ-H2A peptide or a peptide fragment which comprises the C-terminal phosphorylated serine and which is recognizable by an antibody. Similarly, the peptide can be isolated or purified from an organism or synthetically made using methods known in the art. The immunizing peptide can be administered alone, or in a composition further comprising an adjuvant, such as complete or incomplete Freund's adjuvant.

In order to assure that the appropriate antibody or fragment thereof is produced in the immunized animal, blood is taken between immunizations and the serum is assayed for γ-H2A binding specificity. Binding specificity can be determined using an immunoassay such as, for example, ELISA. The antibody or antigenically-reactive fragment thereof may be isolated from the serum by any of a number of separation techniques used in the art, such as, for example, affinity, ion exchange, gel filtration, hydrophobic interaction, and/or protein A affinity chromatography (Harlow et al., *Antibodies, A Laboratory Manual*, Cold Spring Harbor Laboratory Press, Cold Spring, N.Y. (1988)).

Alternatively, monoclonal antibodies may be produced using hybridoma cells. Monoclonal antibodies are a homogenous population of a single antibody clone with defined specificity toward one epitope on an antigen, i.e. the C-terminal phosphorylated serine of an γ-H2A histone protein. The technology for producing monoclonal antibodies is well known (Harlow et al. (1988), supra; and, in general, Roitt et al., *Immunology*, 4$^{th}$ Ed., Mosby, London, England (1996)). Briefly, an animal is immunized with an antigen, i.e., γ-H2A. Lymphocytes are isolated from the spleen or lymph nodes of the immunized animal. Preferably, lymphocytes for preparation of monoclonal antibodies are taken from animals which have demonstrated production of the appropriate antibody. These lymphocytes are fused with an immortal cell line and successfully fused cells are selected for by culturing in HAT medium. The culture supernatants of the resulting hybridoma cells can subsequently be screened for γ-H2A specific antibodies using methods described herein. Culture supernatant containing anti-γ-H2A is collected and the antibody is isolated and purified.

Isolated or purified antibodies or antigenically-reactive fragments thereof of the present invention also can be produced by recombinant techniques (Sambrook et al., *Molecular Cloning*, 2$^{nd}$ Ed., Cold Spring Harbor Laboratory Press, Cold Spring, N.Y. (1989)). For example, recombinant antibodies can be produced by cloning cDNA encoding anti-γ-H2A. The cDNA encoding the appropriate light and heavy chains is incorporated into an expression vector and introduced into a host cell. One of ordinary skill in the art will appreciate that the particular expression vector and regulatory sequences used are not limited as long as the appropriate peptides are produced in the host cell, whether eukaryotic or prokaryotic, and are able to specifically bind γ-H2A. One of ordinary skill in the art will further appreciate that antigenically-reactive fragments also can be produced in this manner. In either case, the expression products are screened for binding specificity using routine methods. Antigenically-reactive antibody fragments also can be generated chemically, e.g., by cleaving an antibody with a protease, such as, for example, pepsin or papain.

In order to detect binding to an γ-H2A protein, the present inventive isolated or purified antibody or antigenically-reactive fragment thereof is, preferably, labeled with a means of facilitating detection. By "means of facilitating detection" is meant that an antibody or fragment thereof is associated with a substrate detectable by conventional, i.e., spectroscopic, biochemical, immunochemical, photochemical or chemical, means. As such, the isolated or purified antibody or antigenically-reactive fragment thereof is preferably labeled with, for example, an enzyme, a radioactive isotope, biotin or a fluorescent molecule, such as fluorescein or rhodamine. Labels may be complexed with the antibody or antigenically-reactive fragment thereof by any means known in the art. For example, a means of detection, such as an enzyme, is biotinylated while the antibody is associated with streptavidin. Biotin and streptavidin bind each other, thereby attaching the label to the antibody. Alternatively, a means of detection can be linked to the antibody via covalent bonding.

Similarly, the present invention provides for fusion proteins comprising an isolated or purified antibody or antigenically-reactive fragment thereof which specifically binds to the C-terminal phosphorylated serine in an H2A histone protein. The isolated or purified antibody or fragment thereof can be fused to an effector protein such as, for example, a toxin or a protein which provides a means of detection of the antibody or fragment thereof. Fusion proteins are constructed using recombinant DNA techniques known in the art (Sambrook et al. (1989), supra). Alternatively, the antibody or antigenically-reactive fragment thereof can be conjugated to an effector molecule. For example, the present inventive antibody can be conjugated to an investigational drug in order to study the effect of the drug on DNA double-stranded breaks.

Also provided by the present invention is a product useful in determining DNA double-stranded breaks. The product comprises an isolated or purified antibody or antigenically-reactive fragment thereof as described herein.

The present invention further provides a method of using an isolated or purified antibody or antigenically-reactive fragment thereof as described herein to determine double-stranded breaks in DNA. The method comprises contacting a sample comprising H2A histone proteins with the antibody or antigenically-reactive fragment thereof, and detecting binding of the isolated or purified antibody or antigenically-reactive fragment thereof to an H2A histone protein in the sample. The detection of the binding of the antibody or antigenically-reactive fragment thereof in the sample indicates the presence of double-stranded breaks in DNA.

By "sample" is meant any sample comprising H2A histone proteins derived from or complexed with DNA, such as in the form of chromatin or reconstituted chromatin. By "derived from" is meant released from DNA, such as chromatin, as a result of natural or unnatural causes. A sample can comprise, for example, a protein extract, such as that used in Western blots or immunoblots. A sample can also comprise whole cells that have been fixed in order to preserve protein structure. Cells may be fixed using, for example, formaldehyde, which preserves protein structure and location within the cells and kills the cells. Cells can then be treated to render the cell membranes permeable to the anti-γ-H2A antibody. The sample can be generated in a laboratory using routine methods or can be derived from an organism. In this regard, cells can be isolated from any source, i.e., blood or tissue samples from an animal, cell samples from yeast, etc.

A sample is contacted with a sufficient amount of antibody or antigenically-reactive fragment thereof for an adequate length of time to allow binding of the antibody to the histone protein. As such, the particular quantity of antibody used in the present inventive method will depend on various factors, such as the size of the sample, the temperature of the reaction, and the affinity of the specific antibody for the antigen. Optimization of binding conditions can easily be determined by the ordinary skilled artisan using routine experimentation.

Preferably, the isolated and purified antibody or antigenically-reactive fragment thereof for use in the present inventive method is labeled with a means of facilitating detection of the binding of the antibody or antigenically-reactive fragment thereof to γ-H2A. Means of facilitating detection include, but are not limited to, an enzyme, a radioactive isotope, a fluorescent molecule, biotin and the like. Alternatively, a labeled secondary antibody can be used to detect binding of the antibody or antigenically-reactive fragment thereof to the H2A histone protein, as discussed below.

Binding of the antibody to the H2A histone protein can be detecting by any number of methods widely used in the art such as, for example, those described in Examples 2, 3 and 4. For instance, antibody binding can be detected using Western blot or immunoblot techniques (see, for example, Frederick et al., *Current Protocols in Molecular Biology*, Wiley Interscience, New York, N.Y. (1987)). Briefly, the antibody of the present invention, the 1° antibody, is allowed to recognize γ-H2A proteins in a sample. Any unbound antibodies are washed away and a labeled 2° antibody is added. The 2° antibody specifically binds to the 1° antibody, thereby identifying 1° antibody-antigen complexes. Any antibody label detectable by conventional means is suitable for the present inventive method. Such labels include, for example, enzymes, such as peroxidase or luceriferase, radioactive isotopes, fluorescent molecules, such as fluorescein or rhodamine, biotin and the like.

Alternatively, a sample of cells, such as cells taken from blood, tissue, etc., is fixed and γ-H2A is assayed directly in the cells by microscopy or cytometry, as illustrated in Example 4 and described in Spector et al., *Cells, A Laboratory Manual*, Cold Spring Harbor Laboratory Press, Cold Spring Harbor, N.Y. (1998). Use of microscopy or cytometry permits the direct measurement of antibody-γ-H2A and, therefore, the number of DNA double-stranded breaks in individual cells. Fluorescent microscopy also enables the determination of the position of a DNA double-stranded break in the nucleus. Measurements from many cells can be automatically tabulated using flow or laser scanning cytometry.

Preferably, the present inventive method further comprises quantifying the amount of double-stranded breaks in DNA. It is believed that, in terms of detection by microscopy, each antibody-γ-H2A foci represents a single double-stranded break in DNA. Therefore, the number of double-stranded breaks present can be counted by counting the foci. This technique requires the use of a high-powered microscope and fluorescently labeled foci. Alternatively, total fluorescence in a sample can be quantified using techniques known in the art, such as, for example, flow or laser cytometry. The fluorescence of a particular sample can be compared to the fluorescence generated by standards comprising a known amount of DNA double-stranded breaks. The amount of DNA double-stranded breaks in the sample can then be estimated. Similarly, the amount of DNA double-stranded breaks can be quantitated from a Western blot or immunoblot using densitometric techniques. Such techniques are widely used in the art. The density of the band corresponding to antibody-γ-H2A complexes on a Western blot can be compared to the density of bands from standards, corresponding samples with known number of breaks, and the number of DNA double-stranded breaks in the sample quantified.

The present inventive method of determining DNA double-stranded breaks has potential widespread applications in a number of fields. For example, the present inventive method is useful to measure the exposure of an organism to a radiation source, e.g., a biological radiation dosimeter. In the medical field, radiation exposure as a cancer treatment is currently measured as radiation output from a particular source. However, a patient is often not exposed to the full quantity of radiation emitted from a source due to scattering, etc. A more precise measurement would be to det ermine the amount of radiation absorbed by the patient, not the amount available to be absorbed. The present inventive method also has utility in monitoring, for example, radiation exposure in workers in nuclear facilities or animals or plants in radiation-contaminated environments. As such, a sample, such as a sample obtained from blood or tissue, can be obtained from an organism and fixed, preferably from about 5 to about 30 minutes, after exposure of the organism to radiation and used in the present inventive method as described above. Preferably, the present inventive method further comprises assessing the extent of an organism's exposure to radiation by comparing the sample with standards exposed to a predetermined amount of radiation. For example, a standard curve can be developed in which matched cells, or cells that are identical to those assayed, are exposed to varying, predetermined amounts of radiation and antibody-γ-H2A quantitated. It is then possible to determine the amount of radiation absorbed in a sample by comparing the amount of γ-H2A of the sample with the standard curve. Such techniques are widely used in the art.

Preferably, the sample is obtained from the organism and fixed at about 15 to about 30 minutes after exposure of the organism to radiation. More preferably, the sample is obtained and fixed at about 30 minutes after exposure of the organism to radiation. A sample can be obtained by any method. A sample is "fixed" in order to prevent degradation (see, for example, *Cell Biology*, (Julio Celis ed.), Academic Press, San Diego, Calif. (1998)). For example, tissue or blood samples that will be used as a source of protein for Western blots are frequently frozen after extraction from an organism and assayed at a later date. The actual proteins extracted from the blood or tissue sample can also be frozen. In some situations, the sample is fixed using formaldehyde, thereby preserving protein structure and location within the cell. By determining the actual amount of radiation absorbed using the method as described above, it is possible to optimize radiation dosage for medical purposes.

Similarly, the present inventive method of detecting DNA double-stranded breaks is useful in determining the sensitivity of an organism to radiation or a mutagen. Sensitivity is measured as the ability to repair DNA double-stranded breaks in response to exposure to radiation or a mutagen. Those organisms more sensitive to, for example, a particular toxin which causes DNA double-breaks would have reduced ability to repair DNA double-stranded breaks as compared to an organism which is not sensitive. The sample to be assayed is from an organism that has been exposed to a mutagen or radiation. The sample can comprise a protein extract taken from blood or tissue cells of an animal, histone proteins isolated from yeast, proteins extracted from cells in culture and the like. The sample can also comprise whole cells that have been made permeable to the present inventive antibody or antigenically-reactive fragment thereof by fixation.

In order to test the sensitivity of an organism to a mutagen or radiation, the present inventive method further comprises assessing the rate of repair of DNA double-stranded breaks by repeatedly contacting a new sample comprising H2A histone proteins with the isolated or purified antibody or antigenically-reactive fragment thereof specific for γ-H2A and detecting binding of the antibody or antigenically-reactive fragment thereof to an H2A histone protein in the sample. The process is repeated one or more times as necessary to assess the rate of repair of DNA double-stranded breaks. A new sample is obtained for each repetition of the process. One of ordinary skill in the art will appreciate that the sensitivity or reaction of an organism, in particular a human, to radiation is useful in tailoring the amount of radiation, for example, in radiation treatment, for a particular individual to achieve maximal therapeutic effect with the minimal amount of radiation.

DNA double-stranded breaks do not result only from radiation exposure, but also from natural cellular processes. The present inventive method is also useful in the study of DNA double-stranded breaks associated with homologous recombination and V(D)J recombination. Homologous recombination is prevalent in many cellular processes, particularly in mitosis and meiosis. Many genetic diseases and disorders, such as certain types of sterility, are linked to chromosomal instability due to homologous recombination. V(D)J recombination is an essential step in the formation of a competent, intact humoral immune system and certain immune deficiency diseases also have been linked to chromosomal instability. The present inventive method of determining DNA double-stranded breaks can aid in the diagnosis and study of such maladies. In the event that the present inventive method is used to determine DNA double-stranded breaks resulting from homologous recombination or V(D)J rearrangement in DNA, detection of binding of the antibody or antigenically-reactive fragment thereof to γ-H2A histone proteins indicates the presence of DNA double-stranded breaks and, therefore, is indicative of homologous recombination or V(D)J recombination in DNA. The method, therefore, aids, for example, in pinpointing the defective step to a cleavage defect or rejoining defect. In determining whether cells defective in homologous or V(D)J recombination form DNA double-stranded breaks, the sample which is contacted with the present inventive antibody or antigenically-reactive fragment thereof can be, for example, protein extracts taken from cells isolated from blood, tissue, or cells in culture. The sample can also be whole cells that have been fixed to preserve protein structure. Preferably, the standard comprises similar cells which are not actively undergoing homologous or V(D)J recombination.

The present inventive method is useful for the study of other natural cellular processes which involve DNA double-stranded breaks aside from homologous recombination. For instance, DNA fragmentation is a classic indicator of apoptosis. Apoptosis, commonly referred to as programmed cell death, is a process wherein cells are systematically degraded into clusters of membrane-bound bodies which are subsequently phagocytized by macrophages or adjacent cells. Thus, the present inventive method is useful as an indicator of apoptosis. One of ordinary skill in the art will appreciate the need for a sensitive assay for DNA double-stranded breaks in apoptosis research. In addition, although part of the cellular lifecycle, apoptosis can also be induced by various drugs to promote cell death. This strategy is most commonly used in the treatment of cancers. The present inventive method, therefore, has utility in determining the effectiveness of a drug to induce apoptosis.

One of ordinary skill in the art will appreciate the need to standardize sample preparation in order to examine accurately apoptosis. Preferably, the sample is taken from a pre-determined quantity of cells in order to reduce variability within measurements. The present inventive method is not dependent on the number of cells in a sample, although the sample must comprise an adequate number of cells to provide enough histone proteins to bind to an isolated or purified anti-γ-H2A antibody or antigenically-reactive fragment thereof and be detectable. A skilled artisan can determine an adequate sample size using routine methods. Similarly, when measuring the effectiveness of a drug to induce apoptosis, samples should be obtained and fixed at set time points after administration of the drug in order to assure uniformity in measurements.

Wherein the present inventive method is used as an indicator of apoptosis, the method further comprises assessing the extent of apoptosis of cells in the sample by comparing the amount of DNA double-stranded breaks detected for the sample to a standard. The greater the signal due to antibody binding to γ-H2A, the greater the incidence of apoptosis. As such, the present inventive method is useful in determining the percentage of cells undergoing apoptosis in a sample. Of course, the standard comprises a sample which, for example, in the case of drug research, has not been exposed to the investigated drug. In the event that the present inventive method is used to study the prevalence of apoptosis in degenerative diseases, the standard comprises cells from an organism free of the disease. A sample and a standard need not be obtained or assayed at the same time. A standard need not be from the same organism from which the sample is taken, although this is preferred.

The present invention also provides a method of determining whether or not cells in a cell sample are in the S phase of the cell cycle. The method comprises obtaining a cell sample that has been exposed to bromodeoxyuridine (BrdU) followed by ultraviolet A (UVA) light. The cells can be isolated from an organism or be cell lines used in research, i.e., MCF7 cells. The cells, preferably in culture, are exposed to BrdU for about 5 to about 60 minutes. BrdU is then incorporated into the DNA of replicating cells in the place of thymidine. The cells are exposed to UVA light, preferably light with a wavelength of about 350 nm to about 400 nm, more preferably having a wavelength of about 365 nm, in the presence of a compound that sensitizes DNA in the cell sample to said UVA light. The compound that sensitizes DNA in the cell sample to UVA light is preferably a dye, such as, for example Hoechst dye, that absorbs energy from the UVA light and transfers that energy to BrdU. The transfer of energy to BrdU subsequently causes a DNA double-stranded break, which leads to the formation of γ-H2A. The method further comprises detecting binding of the present inventive isolated or purified antibody or fragment thereof to an H2A histone protein in the sample. Detection of antibody-γ-H2A binding can be accomplished using any of the methods described herein and illustrated in Examples 2, 3, and 4. Detection of the binding indicates the presence of double-stranded breaks in DNA and, therefore, the presence of cells in the cell sample that are in the S phase of the cell cycle.

The present invention additionally provides a method of determining whether or not cells in a cell sample are in the S phase of the cell cycle comprising the steps of (i) exposing a cell sample to bromodeoxyuridine (BrdU); (ii) exposing the cell sample from (i) to UVA light in the presence of a compound that sensitizes DNA to ultraviolet light; and (iii) detecting binding of the isolated and purified antibody or antigenically-reactive fragment thereof of the present invention to an H2A histone protein in the cell sample. Detecting binding of the antibody or antigenically-reactive fragment thereof to the H2A histone protein can be accomplished using the methods described above. Detection of binding indicates that cells in the cell sample are in S phase.

The use of the present inventive method to determine cell cycle phase can be used in both research and clinical settings. Preferably, the methods are used in the clinical setting and the cell sample is from a patient, in particular a human. The cell sample can be obtained from a patient in any manner and from any source, such as a tumor. In that BrdU is incorporated into actively replicating cells or cells in S phase, the present inventive methods are useful in assessing disorders involving abnormal cellular proliferation. Abnormal cellular proliferation includes cells that undergo rapid and uncontrolled cell proliferation, such as cancer cells, as well as cells that replicate slower than normal, unafflicted cells. The greater the amount of antibody-γ-H2A complexes, the greater the amount of DNA double-stranded breaks. The greater the amount of DNA double-stranded breaks compared to normal, unafflicted cells indicates a greater incidence of cell proliferation in the sample. On the other hand, a decrease in the amount of DNA double-stranded breaks indicates reduced cellular proliferation. The method can be used to assess the efficacy of drugs that promote cell proliferation or factors, such as angiogenic factors. The method also can be used to assess the efficacy of drugs that inhibit cell proliferation.

The present invention also provides a kit for determining DNA double-stranded breaks. The kit comprises an isolated or purified antibody or antigenically-reactive fragment thereof, which specifically binds a C-terminal phosphorylated serine in an H2A protein, as described herein. The kit further comprises a means of detecting binding of the antibody or antigenically-reactive fragment thereof to an H2A histone protein. The kit can be used to perform any of the methods discussed herein.

EXAMPLES

The following examples further illustrate the present invention but, of course, should not be construed as in any way limiting its scope.

Example 1

This example illustrates a preferred method of anti-γ-H2AX antibody production.

The amino acid sequence of H2AX is known in the art and accessible in publicly available databases, i.e., GenBank. A peptide comprising the C-terminal 10 amino acids of H2AX, including the phosphorylated serine, was synthesized using routine methods known in the art. The resulting phosphorylated peptide was analysed by mass spectroscopy and HPLC. High-resolution columns for peptide purification, such as reverse phase Vydac C-8 or C-18 columns (Vydac, Hesperia, Calif.), were used to purify the peptide for administration into rabbits. The purified peptide was conjugated to Keyhole Limpet Hemocyanin, a protein commonly used to couple small haptens, such as peptides, before injection into rabbits.

An initial bleed of New England White Rabbits was performed prior to immunization with 100 μg of peptide in Complete Freund's Adjuvant at day 0 in order to collect pre-immune serum. Subsequent immunizations were administered at day 14, 28 and 42. A first production bleed, approximately 8 to 10 ml, was taken on day 49 and an ELISA was performed using the immunizing peptide to confirm production of an antibody with the appropriate binding specificity. The rabbits were immunized on day 56 and another production bleed was obtained on day 63. The rabbits were again immunized on day 70, after which a third and final production bleed was obtained. Serum from the third bleed was passed through an affinity column containing the unphosphorylated counterpart of the immunizing peptide to absorb antibodies directed to unphosphorylated H2AX. The remaining anti-γ-H2AX antibodies were used in all subsequent experiments.

Example 2

This example demonstrates the ability of anti-γ-H2AX antibodies to bind selectively γ-H2AX.

Immunoblots of protein extracts isolated from various irradiated cell lines were performed using the anti-γ-H2AX antibody prepared in Example 1.

MCF7 human breast cancer and human SF268 astrocytoma cells (NCI Anticancer Drug Screen, Developmental Therapeutics Program) were grown in RPMI 1640 (Gibco BRL #11875, Gaithersburg, Md.) containing 10% fetal bovine serum. Cells were grown in 10 cm dishes, on Labtek II slides or on coverslips and exposed to varying doses of ionizing radiation from a $^{137}$Cs source in a Mark I irradiator (J. L. Shepherd and Associates, San Fernando, Calif.). Doses above 20 Gray (Gy) were given at a rate of 15.7 Gray/min. Doses of 2 and 0.6 Gy were given in one minute.

Following irradiation, cells were lysed and protein extracts were prepared with SDS using methods known in the art. The protein extracts were fractionated on 12% NuPage gels (Novex Novel Technology, San Diego, Calif.) and transferred to a PVDF membrane. The membrane was blocked with 1% dried non-fat milk for 1 hour, then incubated with the anti-γ-H2AX 1° antibody at a 12,000-fold dilution for 2 hours. The membrane was then washed and incubated with peroxidase goat anti-rabbit 2° IgG (Calbiochem-Novabiochem Corp., San Diego, Calif.) at a 3000-fold dilution for 1.5 hours and washed. Anti-γ-H2AX binding was visualized by chemiluminescence (ECL RPN 2209, Amersham Pharmacia Biotech Inc., Piscataway, N.J.).

Immunoblots of total protein extracts from MCF7 cells exposed to 100 Gy of ionizing radiation were incubated with anti-γ-H2AX or preimmune serum in the presence and absence of the immunizing peptide. Anti-γ-H2AX detected one band at the position expected for γ-H2AX. No binding was detected in irradiated samples when the immunizing peptide was present as a competitor or with preimmune serum.

To prove that the antibody was specifically binding γ-H2AX and not unmodified H2AX, protein extracts of irradiated human SF268 astrocytoma cells (100 Gy) were analyzed on high-resolution two-dimensional acetic acid gels which separate γ-H2AX from non-phosphorylated H2AX. Specifically, the acetic acid gels comprise a first acetic acid-urea-Triton X-100 (AUT) dimension followed by a second acetic acid-urea-cetyltrimethylammonium bromide (AUC) dimension (Rogakou et al., *J. Biol. Chem.*, 273, 5858–5868 (1998)). Immunoblots taken from the AUT-AUC gel proved that anti-γ-H2AX bound only to γ-H2AX with no detectable cross-reaction to unmodified H2AX. Also noticeable from the immunoblot was the lack of anti-γ-H2AX binding to H2A1 proteins, whose sequence, except for the C-terminal, is almost identical to H2AX.

The above results indicate that anti-γ-H2AX specifically binds γ-H2AX in the extracts of irradiated cells.

Example 3

This example demonstrates the ability of anti-γ-H2AX to detect homologs of γ-H2AX from other species.

Since the H2AX C-terminus is highly conserved, immunoblots were prepared from irradiated cell cultures of various species to examine whether anti-γ-H2AX could detect γ-H2AX homologs. Indian muntjac, *Muntiacus muntiacus*, normal skin fibroblasts were grown in F-10 Ham's nutrient mixture (Gibco BRL #11550, Gaithersburg, Md.) containing 20% fetal bovine serum. *X. laevis* A6 normal kidney cells were grown in medium NCTC-109 (Gibco BRL #21340, Gaithersburg, Md.) containing 15% deionized water and 10% fetal bovine serum; cultures were maintained at room temperature, about 24° C., in an atmosphere of 5% $CO_2$. *D. melanogaster* epithelial cells were grown in Schneider's Drosophila medium (Gibco BRL #11720, Gaithersburg, Md.) containing 10% heat-inactivated fetal bovine serum at room temperature.

Cultures of *S. cerevisiae* strain BY 4733 were irradiated with 200 Gy of ionizing radiation and allowed to recover for 30 minutes at 30° C. Nuclei were prepared from spheroplasts, and histones extracted as described (Ueda et al., *Dev. Biol.*, 169, 210–217 (1995)). *D. melanogaster* cells were also exposed to 200 Gy of ionizing radiation and extracts were prepared with 0.5 N HCl and fractionated on 12% AUT gels. *M. muntiacus* and *X. laevis* cells were exposed to 100 Gy of radiation and fractionated on 12% NuPage SDS gels (Novex, San Diego, Calif.).

Immunoblots were prepared as described in Example 2. Anti-γ-H2AX detected one band that migrated as expected for the appropriate γ-H2AX homolog, not only in other examined mammalian species, such as mouse, rat, hamster and deer (*M. muntiacus*), but also in the African clawed toad (*X. laevis*), fruit fly (*D. melanogaster*) and in budding yeast (*S. cerevisiae*).

This example establishes the ability of anti-γ-H2AX to bind not only mammalian γ-H2AX, but γ-H2AX homologs from other species.

Example 4

This example demonstrates the determination of DNA double-stranded breaks with the anti-γ-H2AX antibody.

It was hypothesized that each γ-H2AX focus identifies a DNA double-stranded break. In order to determine this, advantage was taken of the finding that γ-H2AX was formed when DNA double-stranded breaks were introduced into cells by the BrdU-dye-UVA light procedure of Limoli et al. (*Radiation Research*, 134, 160–169 (1993)). MCF-7 cells, grown in the presence or absence of 0.4 μM BrdU and 2.4 μM thymidine for 3 days, were subcultured onto coverslips that had been gently scribed with lines by a diamond pencil. After growth for 24 hours, the cells were incubated with Hoechst dye 33258 (Sigma, St. Louis, Mo.) for 5 minutes. The coverslips were mounted on a glass slide with a 0.5 mm thick silicone gasket (Electron Microscopy Sciences, Fort Washington, Pa.) to form a chamber which was filled with PBS. The slides were kept on ice until placed on the stage of the microscope fitted with a LaserScissors$^{TM}$ Module 390/20 (Cell Robotics, Inc., Albuquerque, N. Mex.). This laser emits at 390 nm, a wavelength at which the Hoechst dye has substantial absorption and has the advantage of permitting the illumination of specific partial nuclear volumes. An image of the chosen field of cells containing an inscribed line was recorded and printed. A proposed path of the laser was traced on the print. The laser was operated at various power outputs (100%=20 μj/pulse) and focused through a 100× objective to a 0.5 μm diameter circle in the focal plane of the cells with the pulse rate set at 10 pulses per second. The laser was guided by means of a joystick along the traced path at a maximum rate of 8 μm per second. After irradiation, the coverslips were transferred to a culture dish with growth media for 30 minutes at 370° C. before fixation. After processing for laser scanning confocal microscopy, the coverslips were mounted on slides and the irradiated cell groupings found with the aid of the inscribed lines.

The cell preparations were fixed in 2% paraformaldehyde in PBS for 5 minutes, washed in PBS, permeabilized in 100% methanol at −20° C. for 5 minutes and washed. The sample was blocked with 8% BSA for 1 hour, incubated with the anti-γ-H2AX 1° antibody at 800-fold dilution for 2 hours and washed. The sample was then incubated with a Cy2-conjugated goat anti-rabbit 2O° antibody (Jackson Immunolabs, West Grove, Pa.) at 200-fold dilution for 1 hour, washed and mounted with or without propidium iodide. Cy2 is a cyanine fluorescent dye similar in spectra to FITC. Experiments were also performed using FITC-conjugated 2° antibody with similar results. Cell preparations were viewed with a PCM2000 laser scanning confocal microscope (Nikon, Inc., Melville, N.Y.) using a loox objective. Optical sections (0.5 mm) through the thickness of the sample were imaged and combined in a maximum projection with Simple32 software (Compix, Inc., Imaging Systems, Cranberry Township, Pa.) so that all the visible foci and bands in a nucleus or mitotic figure were recorded. The projection was saved as a BMP file and brought into Paint Shop Pro 5 (Jase Software, Inc., Eden Prairie, Minn.) and Powerpoint (Microsoft Corp., Redlands, Wash.) for presentation.

When MCF-7 cells with BrdU-containing DNA were exposed to the laser in the presence of dye, those nuclear regions traversed by the laser at 1%, 10% and 30% relative power contained antibody-γ-H2AX foci. Antibody-γ-H2AX formation was dependent on the presence of BrdU; when BrdU was absent but dye still present, antibody-γ-H2AX foci were consistently found only the cells traversed with the laser at 30% relative power.

This example demonstrates that antibody-γ-H2AX foci form at the sites of DNA double-strand breaks.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

---

---

What is claimed is:

1. An isolated or purified antibody or antigenically-reactive fragment thereof that binds to a C-terminal amino acid sequence of an H2A histone protein, said C-terminal amino acid sequence consisting of SQ(D/E/A)(I/L/Y/F) (SEQ ID NO: 1) that comprises a phosphorylated serine, wherin the antibody or antigenically reactive fragment thereof does not detectably bind to a C-terminal amino acid sequence of an H2A histone protein, said C-terminal amino acid sequence consisting of SQ(D/E/A)(I/L/Y/F) (SEQ ID NO: 1) that does not comprise a phosphorylated serine under conditions when the isolated or purified antibody or antigenically-reactive fragment thereof binds to the C-terminal amino acid sequence of an H2A histone protein, C-terminal amino acid sequence consisting of SQ(D/E/A) (I/L/Y/F) (SEQ ID NO: 1) that comprises a phosphorylated serine.

2. The isolated or purified antibody or antigenically-reactive fragment thereof of claim 1, wherein said phosphorylated serine is about four amino acids from the C-terminus of said H2A histone protein.

3. The isolated or purified antibody or antigenically-reactive fragment thereof of claim 1, wherein said antigenically-reactive fragment is selected from the group consisting of Fab, Fab', F(ab')$_2$, and F(v).

4. The isolated or purified antibody or antigenically-reactive fragment thereof of claim 1, wherein said H2A histone protein is mammalian.

5. The isolated or purified antibody or antigenically-reactive fragment thereof of claim 4, wherein said H2A histone protein is H2AX.

6. The isolated or purified antibody or antigenically-reactive fragment thereof of claim 1, wherein said antibody or fragment thereof is labeled with a means for facilitating detection.

7. The isolated or purified antibody or antigenically-reactive fragment thereof of claim 6, wherein said means for facilitating detection is an enzyme, a radioactive isotope, a fluorescent molecule, or biotin.

8. A composition comprising an isolated or purified antibody or antigenically-reactive fragment thereof of any of claims 1, 2 or 3–7.

9. A fusion protein comprising the isolated or purified antibody or antigenically-reactive fragment thereof of claim 1.

10. The isolated or purified antibody or antigenically-reactive fragment thereof of claim 1, the binding of which to the C-terminal amino acid sequence of an H2A histone protein, said C-terminal amino acid sequence consisting of SQ(D/E/A)(I/L/Y/F) (SEQ ID NO: 1) that comprises a phosphorylated serine is detected via chemiluminescence using an enzyme-linked antibody that binds to the isolated or purified antibody or antigenically-reactive fragment thereof.

* * * * *

SEQUENCE LISTING

```
<160> NUMBER OF SEQ ID NOS: 1

<210> SEQ ID NO 1
<211> LENGTH: 4
<212> TYPE: PRT
<213> ORGANISM: Unknown Ogranism
<220> FEATURE:
<223> OTHER INFORMATION: Description of Unknown Organism: Mammal
<221> NAME/KEY: misc_feature
<222> LOCATION: (3)..(3)
<223> OTHER INFORMATION: "Xaa" may be "Asp," "Glu," or "Ala"
<221> NAME/KEY: misc_feature
<222> LOCATION: (4)..(4)
<223> OTHER INFORMATION: "Xaa" may be "Ile," "Leu," "Tyr," or "Phe"

<400> SEQUENCE: 1

Ser Gln Xaa Xaa
```